(12) United States Patent
Thompson

(10) Patent No.: US 6,319,529 B1
(45) Date of Patent: Nov. 20, 2001

(54) SELENIUM DIET SUPPLEMENT AND METHOD OF MAKING

(75) Inventor: Leif H. Thompson, Philo, IL (US)

(73) Assignee: Thompson Animal Systems, Inc., Philo, IL (US)

(*) Notice: Subject to any disclaimer, the term of this patent is extended or adjusted under 35 U.S.C. 154(b) by 0 days.

(21) Appl. No.: 09/636,331

(22) Filed: Aug. 10, 2000

Related U.S. Application Data

(60) Provisional application No. 60/148,555, filed on Aug. 12, 1999.

(51) Int. Cl.$^7$ ............................................. A23L 1/304
(52) U.S. Cl. ............................ 426/74; 426/615; 426/648; 426/809
(58) Field of Search ............................... 426/74, 615, 648, 426/809

(56) References Cited

U.S. PATENT DOCUMENTS

| | | | |
|---|---|---|---|
| 5,785,977 | * | 7/1998 | Breithbarth .................. 424/401 |
| 6,117,462 | * | 9/2000 | Ensley et al. .................. 426/74 |

FOREIGN PATENT DOCUMENTS

1251264 A * 4/2000 (CN).

\* cited by examiner

*Primary Examiner*—Helen Pratt
(74) *Attorney, Agent, or Firm*—Philip L. Bateman

(57) ABSTRACT

A diet supplement improves the growth and health of humans and other animals. The supplement contains: (1) germs having a selenium level of at least about 0.2 ppm that are derived from a cereal grain grown in selenium-rich soil; and (2) plant materials having a selenium level of at least about 0.2 ppm that are from a legume grown in selenium-rich soil.

6 Claims, No Drawings

SELENIUM DIET SUPPLEMENT AND METHOD OF MAKING

CROSS-REFERENCE TO RELATED APPLICATION

This application claims the benefit of U.S. Provisional Application Ser. No. 60/148,555, filed Aug. 12, 1999.

FIELD OF THE INVENTION

This invention relates to diet supplements for humans and other animals. More particularly, this invention relates to diet supplements that contain selenium, Vitamin A, Vitamin E, folic acid, and fiber.

BACKGROUND OF THE INVENTION

Diet plays a major role in the growth and health of humans and other animals. Nutrients in the diet perform three primary functions in the body. They provide the materials for building, repairing, and maintaining body tissues; they help regulate body processes; and they serve as fuel to provide energy. Nutrients are often classified into five main groups: (1) carbohydrates; (2) fats; (3) proteins; (4) minerals; and (5) vitamins. For humans, the Food and Nutrition Board of the U.S. National Academy of Sciences has established Minimum Dietary Allowances (MDA) and Recommended Dietary Allowances (RDA) for a large number of nutrients. Although not nutrients, other components of the diet are also important. For example, water is essential for life and dietary fiber is necessary for the efficient functioning of the digestive system.

Selenium is an element of atomic number 34. It is considered one of the essential trace minerals in the human diet. Selenium is believed to be essential for the proper development and functioning of the heart. Selenium is also a key component of the blood cell enzyme glutathione peroxidase that is, in turn, believed to be an anti-oxidant. Anti-oxidants are molecules that scavenge, or remove, free radicals. Free radicals are molecules with a lone pair of electrons that are highly reactive and are believed to play a role in cancer. The sale of selenium dietary supplements has dramatically increased over the past few years. Most of the selenium dietary supplements are derived from artificial sources such as yeast cultures.

An excess of selenium is believed to be as deleterious as an insufficiency. Excess selenium causes damage to various organs, especially the liver, and can cause death. It is believed that the damage from excess selenium results from selenium's interference with the sulfur-sulfur bonds in proteins. Although the MDA and RDA for selenium have not been established, the U.S. Food and Drug Administration (FDA) has expressed concern about the excessive use of selenium dietary supplements. The FDA has recommended that the maximum daily intake should not exceed 150 micrograms of organic selenium.

Selenium is present in the soil, but the level of selenium in the soil varies widely around the world. In most parts of the world, the level of selenium in the soil is about 0.01 to 0.05 parts per million by weight (ppm) or lower. However, in some parts of the world, the level of selenium is much greater. In some parts of the Western United States, including all or parts of the states of Montana, South Dakota, Wyoming, Utah, Nevada, California, Arizona, and New Mexico, the level of selenium in the soil is about 1 to 5 ppm or greater. This level is about 100 times the level of selenium in most parts of the world.

The level of selenium in the soil is important because it directly affects the level of selenium in crops grown in the soil, and, through the food chain, the level of selenium in animals who eat the crops. The uptake of selenium by plants depends on the type of plant and on the pH of the soil. Selenium in alkaline soils is in the form of selenates that are readily taken up by plants, but selenium in neutral or acidic soils is in the form of selenites that are unavailable to plants.

Cereal grains are grasses that are grown and harvested for food. Cereal grains include wheat, rice, corn, barley, sorghum, oats, rye, millet, and buckwheat. The terms "cereal" and "grain" are used interchangeably. The edible portion of cereal grains is the seed, also known as the kernel. The seed typically consists of an outer coat, a germ (or embryo) that contains most of the seed's protein, and an endosperm that contains a large quantity of starch that serves as the source of energy for the embryo. Some cereal grains are eaten directly by humans after cooking, but most are first milled and/or processed into flour, meal, starch, and other forms.

Cereal grains contain selenium when grown in alkaline soils containing selenium. The selenium in cereal grains concentrates in the germ because selenium in the organic state is normally associated with protein. For example, when wheat is grown in selenium-rich soil, the level of selenium in the seed as a whole is at least about 0.2 ppm. If the seed is milled and separated into components, the level of selenium in the germ is typically several times greater.

Legumes are flowering plants that are instrumental in nitrogen fixation. Nitrogen fixation is the process by which nitrogen is taken from the atmosphere and converted to organic compounds that can be used by plants. Legumes are often raised for food. With some legumes, such as peas, beans, soybeans, and peanuts, only the seed pods are eaten. With other legumes, such as alfalfa, clover, and vetch, livestock and humans eat other components of the plant, including the leaves, stems, and flowers. These components are known collectively as plant material. Legumes appear to be very effective at uptaking selenium from the soil. For example, vetch grown in an alkaline selenium-rich soil can contain up to about 200 ppm selenium and can cause death to livestock if eaten in quantity.

Cereal grains, legumes, and their various constituent factions have been used as foods for humans and animals since prehistoric times. The use of selenium as a diet supplement for humans and animals, although recent, is also well known. However, a demand exists for an economical supplement to add selenium, Vitamin A, Vitamin E, folic acid, and fiber to the human diet.

SUMMARY OF THE INVENTION

The general object of this invention is to provide an improved diet supplement for humans and other animals.

I have invented an improved diet supplement for humans and other animals. The supplement comprises: (1) germs having a selenium level of at least about 0.2 ppm that are derived from a cereal grain grown in selenium-rich soil; and (2) plant materials having a selenium level of at least about 0.2 ppm that are from a legume grown in selenium-rich soil.

The combination of the selenium-rich germ and legume produces a significant improvement in the effect on the bodies of humans and other animals.

DETAILED DESCRIPTION OF THE INVENTION

The diet supplement of this invention comprises two components. The first components are germs having a selenium level of at least about 0.2 ppm, preferably at least about 0.5 ppm, that are derived from the seeds of cereal grains grown in selenium-rich soil. The second components are plant materials having a selenium level of at least about 0.2 ppm, preferably at least about 0.5 ppm, that are from legumes grown in selenium-rich soil. The term "selenium-rich soil" is used herein to refer to alkaline soils having a level of selenium of at least about 1 ppm. Selenium-rich soils are present in much of the States of Montana, South Dakota, Wyoming, Utah, Nevada, California, Arizona, and New Mexico.

Germs from the seeds of cereal grains such as wheat, rice, corn, barley, sorghum, oats, rye, millet, and buckwheat are suitable. Other components of the seed, such as the endosperm and outer coat, may also be present with the germ. However, it is preferred that the amount of these other components be minimized because they generally do not contain as high levels of selenium as the germ. The preferred cereal grain is wheat for several reasons. First, the level of selenium is especially greater in wheat germ. Second, wheat germ is also high in Vitamin E, an essential nutrient that is also an effective anti-oxidant. It is believed that selenium and Vitamin E provide synergistic anti-oxidizing effects. And third, wheat germ is available in great quantity at a relatively low cost.

Suitable legumes include alfalfa, clover, and vetch. The preferred legume is alfalfa because it is high in Vitamin A, folic acid, fiber and other nutrients, and because it is available in great quantity at a relatively low cost.

The supplement contains a weight ratio of germ to legume of about 10:1 to 1:10. The weight ratio of germ to legume is preferably about 2:1 to 1:2 and is most preferably about 1:1.

For humans, the supplement is preferably ingested in an amount of about 2 to 4 g per day. As an illustrative example, assuming the germ contains 5.0 ppm selenium, the legume contains 1.0 ppm selenium, the weight ratio of germ to legume is 1:1, and the supplement contains only germ and legume plant material, ingesting 3.0 g of the supplement each day provides about 9 micrograms of selenium, or about six percent of the FDA's recommended maximum daily intake of 150 micrograms.

For humans, the supplement is preferably ingested by itself in one of various forms, including pelletized tablet, powder, and capsule. For other animals, the supplement is preferably combined with a feed.

The following example is illustrative only.

EXAMPLE 1

This example illustrates the effect of selenium content in wheat germ and alfalfa on growth, feed performance, and glutathione peroxidase activity in baby chickens.

Samples of wheat germ and alfalfa from selenium-poor soil in Illinois, a low selenium source (LS), and from selenium-rich soil in Wyoming, a high selenium source (HS), were obtained for chemical analysis and used in diets for baby chickens. Test diets were made from a basal diet of corn/soybean meal developed by poultry scientists at the Poultry Research Complex at the University of Illinois by replacing six pounds of soybean meal (of the 50 pound quantity) with four pounds of wheat germ from either LS or HS sources and six pounds of ground alfalfa from either LS or HS source. The final test diets contained 54 pounds rather that the original 50 pounds because of the addition of alfalfa which is less digestible than an equal quantity of soybean meal.

Diet 1 contained low selenium wheat germ and low selenium alfalfa, and analyzed at 0.135 ppm selenium. Diet 2 contained high selenium wheat germ and low selenium alfalfa, and analyzed at 0.162 ppm selenium. Diet 3 contained low selenium wheat germ and high selenium alfalfa, and analyzed at 0.229 ppm selenium. Diet 4 contained high selenium wheat germ and high selenium alfalfa, and analyzed at 0.250 ppm selenium. Selenium levels of the individual feed ingredients and diets are contained in Table 1. All analyses were done at Olson Biochemistry Lab at South Dakota State University, Brookings, S.Dak.

TABLE 1

Selenium Content of Various Feed Ingredients and Diets

| Item | Level of selenium (ppm) |
|---|---|
| Illinois wheat germ (LS) | 0.166 |
| Wyoming wheat germ (HS) | 0.601 |
| Illinois alfalfa (LS) | 0.041 |
| Wyoming alfalfa (HS) | 0.802 |
| Basal diet of corn-soybean meal | 0.161 |
| Diet 1 LS wheat germ, LS alfalfa | 0.135 |
| Diet 2 HS wheat germ, LS alfalfa | 0.162 |
| Diet 3 LS wheat germ, HS alfalfa | 0.229 |
| Diet 4 HS wheat germ, HS alfalfa | 0.250 |

The diets were prepared at the University of Illinois Poultry Research Complex. The basal diet was prepared from a vitamin and trace mineral premix which contained no added selenium and no added vitamin E.

In the experiment, newly-hatched chicks were fed the basal diet for three days before being weighed for allotment to one of the four treatments. Fifty-six birds were selected and assigned to eight pens in a battery, seven birds per pen on the basis of initial weight. Each pen contained birds of the same range of weights. Beginning at day three, birds were fed their respective diets for a total of 24 days. Body weights were taken weekly and at the end of the experimental period. Feed consumption was measured. Temperature was maintained at approximately 82° F. for the first 10 days of the test and was allowed to deviate more normally after that time. At the last weight determination, a 5 cc blood sample was obtained by cardiac puncture. Whole blood was centrifuged at 3800 rpm for 15 minutes, and serum was collected and shipped on dry ice to the University of Kentucky Graduate Center for Toxicology, Lexington, Ky. for analysis of glutathione peroxidase activity. This is reportedly the most definitive assay for dietary selenium availability. The method used for determining glutathione peroxidase activity is described by Paglio and Valentine (1967) in the *Journal of Laboratory Clinical Medicine* 70:158. Glutathione peroxidase activity is measured in units of nanomoles per minute per milligram (nmol/min/mg). Samples from five of the seven birds in each pen were used in the analysis. Tube numbers were completely randomized to mask treatment identity.

Following analysis for glutathione peroxidase activity, identification of bird number with tube number was revealed to facilitate a statistical analysis of the data by treatments. All data were expressed as mean±SE with n=10 for each group (Diet). Data were analyzed by ANOVA. In cases where the ANOVA produced significant interesting data, further analyses were done using Fisher's LSD procedure.

Chemical analyses of the ingredient sources by scientists at South Dakota State University revealed that selenium of the HS wheat germ from hard red winter wheat was approximately four fold higher than LS wheat germ from soft winter wheat. Also, HS alfalfa contained a great deal more selenium that LS alfalfa. Content of the HS alfalfa was approximately 20 fold higher than LS alfalfa. As a result, the diets as shown in Table 1 contained varying amounts of selenium which were directly related to the varying ingredient sources. Diet 1, which was intended to be a low selenium diet, contained about half the selenium level as the diet with both HS wheat germ and HS alfalfa. The results of the experiment are shown in Table 2.

TABLE 2

Effect of Selenium Content of Diet on Chick Performance, Feed Consumption and Efficiency of Feed Conversion

|  | Diet 1 | Diet 2 | Diet 3 | Diet 4 |
| --- | --- | --- | --- | --- |
| Number of birds | 14 | 14 | 14 | 14 |
| Initial wt (grams) | 79 | 79 | 79 | 79 |
| Final wt (grams) | 652 | 657 | 654 | 671 |
| Total gain (grams) | 573 | 578 | 575 | 592 |
| Total feed (grams) | 1,014 | 1,040 | 1,004 | 1,034 |
| Feed/gain | 1.770 | 1.799 | 1.746 | 1.747 |

The total gain of the chicks receiving Diet 4 was sizable when considering the fact that the basal diet was not as selenium deficient as was desired. Furthermore, addition of wheat germ with its inherent high levels of vitamin E would have greatly lessened the impact of the higher selenium level observed in the two ingredients from HS sources. The greatest improvement in gain was noted in the diets with high selenium content. In support of the biology of a balanced diet, feed efficiency was slightly higher also in the two diets with the high selenium level, Diets 3 and 4. These results might be completely reversed; in other words, the high selenium diets might have caused reduced gain and poor feed efficiency if the dietary content had approached the toxic level. Even though selenium is an essential nutrient, it is required in very small or even minute quantities. When present in the diet or drinking water at slightly higher levels, it becomes quite toxic and can cause death as well as many other deleterious side effects in most herbivores. The safety range between dietary need and toxic level of selenium is among the very narrowest of all micronutrients. As a result of the very narrow range of tolerance, the positive difference noted in both gain and feed efficiency is sizable and consistent with level of selenium measured in the four test diets. It is entirely possible that the high level of vitamin E might help improve the efficiency of selenium as a nutrient source and provide some safety against the deleterious effects of possible selenium toxicity. This combination of a high level of vitamin E with a high selenium source appears to be of unique nutritional value. As a result, dietary safety of a selenium source may be enhanced by including high vitamin E because of the synergistic action biologically of the two nutrients.

While the concept of body growth and feed efficiency are very general and broadly based biological reactions, a bioassay which is extremely specific for selenium availability in the diet would provide greater clarity for accurate evaluation. Glutathione peroxidase is the definitive assay and an enzyme which contain stoichiometric amounts of selenium in the form of selenocysteine residues. The ability of glutathione peroxidase to reduce various hydrogen peroxides has led to the proposal of the enzyme in protecting tissues against oxidative damage to membranes and other large molecular structures. Results of the biochemical and statistical analyses were combined and are presented in Table 3.

All activities are expressed as mean±SE with n=10 for each group. All mean activities are different at 0.001.

TABLE 3

Effect of Dietary Source of Selenium on Selenium Dependent Glutathione Peroxidase Activity

| Diet | Activity (nmol/min/mg) |
| --- | --- |
| Diet 1 LS wheat germ, LS alfalfa | 1.274 ± 0.383 |
| Diet 2 HS wheat germ, LS alfalfa | 2.038 ± 0.293 |
| Diet 3 LS wheat germ, HS alfalfa | 2.436 ± 0.943 |
| Diet 4 HS wheat germ, HS alfalfa | 2.657 ± 0.974 |

The birds in Treatment 1 contained significantly lower levels of glutathione peroxidase (GPX) while the level of GPX in each successive treatment was highly, highly different significantly at the 0.001 level. These results suggest extreme clarity of treatment differences when one considers the level of confidence in the statistical analysis. Generally, results are deemed reliable when statistical differences are noted at the 5% or 1% levels. Furthermore, the mean levels from Treatment 1 to Treatment 4 have more than doubled leading to the suggestion that the level of selenium in Diets 3 and 4 might have been more available in addition to being present at a higher level. The resulting dramatic increase in glutathione peroxidase activity by including both wheat germ and alfalfa from high seleniferous soils in Wyoming was not expected, certainly not to such a degree of statistical significance.

The experiment illustrates the following. First, the growth rate of baby chicks was slightly improved and feed efficiency was somewhat greater when baby chicks were fed wheat germ and alfalfa from high selenium sources as compared to low selenium sources. Second, dietary toxicity of selenium was not apparent in any diet. Third, glutathione peroxidase activity was improved at a much higher level statistically in serum of birds fed the diets containing the HS wheat germ and alfalfa. The level of activity and accuracy of the test were far greater than expected.

I claim:

1. A diet supplement for humans and other animals, the supplement comprising: (1) germs having a selenium level of at least about 0.2 ppm that are derived from a cereal grain grown in selenium-rich soil; and (2) plant materials having a selenium level of at least about 0.2 ppm that are from a legume grown in selenium-rich soil.

2. The diet supplement of claim 1 wherein the germs are from wheat.

3. The diet supplement of claim 2 wherein the plant material comprises leaves and stems from alfalfa.

4. A method of improving the health of humans and other animals, the method comprising adding to the diet a supplement comprising: (1) germs having a selenium level of at least about 0.2 ppm that are derived from a cereal grain grown in selenium-rich soil; and (2) plant materials having a selenium level of at least about 0.2 ppm that are from a legume grown in selenium-rich soil.

5. The method of claim 3 wherein the germs are from wheat.

6. The method of claim 4 wherein the plant material comprises leaves and stems from alfalfa.

* * * * *